US012692300B2

(12) United States Patent
     Lee

(10) Patent No.: US 12,692,300 B2
(45) Date of Patent: Jul. 28, 2026

(54) METHOD FOR TREATING SARS-COV-2 INFECTIOUS DISEASE

(71) Applicant: RESEARCH & BUSINESS FOUNDATION SUNGKYUNKWAN UNIVERSITY, Suwon-si (KR)

(72) Inventor: Wonhwa Lee, Suwon-si (KR)

(73) Assignee: RESEARCH & BUSINESS FOUNDATION SUNGKYUNKWAN UNIVERSITY, Suwon-si (KR)

( * ) Notice: Subject to any disclaimer, the term of this patent is extended or adjusted under 35 U.S.C. 154(b) by 615 days.

(21) Appl. No.: 18/181,881

(22) Filed: Mar. 10, 2023

(65) Prior Publication Data

US 2023/0406913 A1      Dec. 21, 2023

(30) Foreign Application Priority Data

Mar. 11, 2022    (KR) ........................ 10-2022-0030971

(51) Int. Cl.
| | |
|---|---|
| *C07K 16/18* | (2006.01) |
| *A61K 39/395* | (2006.01) |
| *A61P 31/12* | (2006.01) |
| *C07K 16/22* | (2006.01) |
| *C12N 15/113* | (2010.01) |
| *C12Q 1/6844* | (2018.01) |
| *C12Q 1/70* | (2006.01) |
| *G01N 33/569* | (2006.01) |
| *G01N 33/68* | (2006.01) |
| *A61K 39/00* | (2006.01) |

(52) U.S. Cl.
CPC .......... *C07K 16/18* (2013.01); *A61K 39/3955* (2013.01); *C07K 16/22* (2013.01); *C12N 15/113* (2013.01); *C12N 15/1136* (2013.01); *C12Q 1/6844* (2013.01); *C12Q 1/701* (2013.01); *G01N 33/56983* (2013.01); *G01N 33/6893* (2013.01); *A61K 2039/505* (2013.01); *C12N 2310/11* (2013.01); *C12N 2310/14* (2013.01); *C12N 2310/141* (2013.01); *C12N 2310/16* (2013.01); *C12N 2310/20* (2017.05); *C12Q 2600/112* (2013.01); *C12Q 2600/118* (2013.01); *C12Q 2600/158* (2013.01); *C12Q 2600/178* (2013.01); *G01N 2333/165* (2013.01); *G01N 2333/475* (2013.01); *G01N 2469/10* (2013.01)

(58) Field of Classification Search
CPC .. C07K 2317/76; C07K 14/475; C07K 16/22; C12N 15/113; C12N 15/1136; C12N 2310/11; C12N 2310/14; C12N 2310/141; C12N 2310/16; C12N 2310/20; C12Q 1/6844; C12Q 2600/158; C12Q 2600/178; C12Q 2600/118; C12Q 2600/112; G01N 33/6893; G01N 33/68; G01N 2333/475; G01N 2333/165; A61K 39/3955; A61K 2039/505; A61P 31/12
See application file for complete search history.

(56) References Cited

U.S. PATENT DOCUMENTS

2022/0000481 A1    1/2022  Sung et al.

FOREIGN PATENT DOCUMENTS

| | | |
|---|---|---|
| KR | 10-2367980 B1 | 3/2022 |
| WO | WO 2020/223647 A1 | 11/2020 |

OTHER PUBLICATIONS

Adamo et al. Signature of long-lived memory CD8+ T cells in acute SARS-CoV-2 infection. Nature 602(7895): 148-155, 2021.*
Agrawal et al. Computer-Aided Discovery of Small Molecule Inhibitors of Thymocyte Selection-Associated High Mobility Group Box Protein (TOX) as Potential Therapeutics for Cutaneous T-Cell Lymphomas. Molecules 24: 3459, 2019; doi:10.3390/molecules24193459 (14 total pages).*
Alahdal et al. Exhaustion and over-activation of immune cells in COVID-19: Challenges and therapeutic opportunities. Clin Immunol 245: 109177, 2022 (11 total pages).*
Alfei et al. TOX reinforces the phenotype and longevity of exhausted T cells in chronic viral infection. Nature 571: 265-269, 2019.*
Brauneck et al. Increased frequency of TIGIT+CD73-CD8+ T cells with a TOX+ TCF-1low profile in patients with newly diagnosed and relapsed AML. OncoImmunol 10(1): e1930391, 2021 (13 total pages).*
Diao et al. Reduction and Functional Exhaustion of T Cells in Patients With Coronavirus Disease 2019 (COVID-19). Front Immunol 11: 827, 2019 (7 total pages).*
Dulmage et al. Dysregulation of the TOX-RUNX3 pathway in cutaneous T-cell lymphoma. Oncotarget 10(33): 3104-3113, 2019.*
El-Hamd Neinaa et al. TOX as a diagnostic and prognostic marker for mycosis fungoides. J Egypt Women Dermatol Soc 15: 15-22, 2018.*
Khan et al. TOX transcriptionally and epigenetically programs CD8+ T cell exhaustion. Nature 571: 211-218, 2019 (24 total pages).*

(Continued)

*Primary Examiner* — Bridget E Bunner
(74) *Attorney, Agent, or Firm* — LEX IP MEISTER, PLLC

(57) ABSTRACT

Disclosed are a composition for diagnosis of SARS-CoV-2 infectious disease, a diagnostic kit, a method for providing information for diagnosis, a method for screening a therapeutic agent, and a composition for prevention or treatment, wherein it is expected that the diagnosis or prognostic prediction of the severity of SARS-CoV-2 infectious disease can be attained and the control of expression and activity of TOX, which is a marker, can be advantageously used in the development of a therapeutic agent for SARS-CoV-2 infectious disease.

3 Claims, 8 Drawing Sheets

Specification includes a Sequence Listing.

(56)            References Cited

OTHER PUBLICATIONS

Kim et al. The TOX-RAGE axis mediates inflammatory activation and lung injury in severe pulmonary infectious diseases. Proc Natl Acad Sci USA 121(26): e2319322121, 2024 (10 total pages).*

Liang et al. TOX as a potential target for immunotherapy in lymphocytic malignancies. Biomarker Res 9:20, 2021 (8 total pages).*

Maurice et al. Inflammatory signals are sufficient to elicit TOX expression in mouse and human CD8+ T cells. JCI Insight 6(13): e150744, 2021 (15 total pages).*

Song et al.Treatment with soluble CD24 attenuates COVID-19-associated systemic immunopathology. J Hematol Oncol 15: 5, 2022; doi.org/10.1186/s13045-021-01222-y (31 total pages).*

Wang et al. TOX promotes the exhaustion of antitumor CD8+ T cells by preventing PD1 degradation in hepatocellular carcinoma. J Hepatol 71: 731-741, 2019.*

Xu et al. Molecular profiling of TOX-deficient neoplastic cells in cutaneous T cell lymphoma. Arch Dermatol Res 312: 513-525, 2020.*

Rha, Min-Seok, et al. "Activation or exhaustion of CD8+ T cells in patients with COVID-19." Cellular & molecular immunology 18.10 (2021): 2325-2333.

Korean Office Action issued on Aug. 24, 2023, in counterpart Korean Patent Application No. 10-2022-0030971 (4 pages in Korean, 3 pages in English).

Maestre, Lorena, et al. "High-mobility group box (TOX) antibody a useful tool for the identification of B and T cell subpopulations." PLoS One 15.2 (2020): e0229743, (16 pages).

Korean Office Action issued on Dec. 20, 2023, in counterpart Korean Patent Application No. 10-2022-0030971 (1 page in English, 2 pages in Korean).

* cited by examiner

SARS-CoV-2 Non-ICU
Low TOX in plasma

SARS-CoV-2 ICU
High TOX in Plasma

SEQUENCE LISTING

```
Sequence total quantity: 2
SEQ ID NO: 1          moltype = AA  length = 526
FEATURE               Location/Qualifiers
REGION                1..526
                      note = TOX(Thymocyte Selection Associated High Mobility
                      Group Box)
source                1..526
                      mol_type = protein
                      organism = synthetic construct
SEQUENCE: 1
MDVRFYPPPA QPAAAPDAPC LGPSPCLDPY YCNKFDGENM YMSMTEPSQD YVPASQSYPG  60
PSLESEDFNI PPITPPSLPD HSLVHLNEVE SGYHSLCHPM NHNGLLPFHP QNMDLPEITV  120
SNMLGQDGTL LSNSISVMPD IRNPEGTQYS SHPQMAAMRP RGQPADIRQQ PGMMPHGQLT  180
TINQSQLSAQ LGLNMGGSNV PHNSPSPPGS KSATPSPSSS VHEDEGDDTS KINGGEKRPA  240
SDMGKKPKTP KKKKKKDPNE PQKPVSAYAL FFRDTQAAIK GQNPNATFGE VSKIVASMWD  300
GLGEEQKQVY KKKTEAAKKE YLKQLAAYRA SLVSKSYSEP VDVKTSQPPQ LINSKPSVFH  360
GPSQAHSALY LSSHYHQQPG MNPHLTAMHP SLPRNIAPKP NNQMPVTVSI ANMAVSPPPP  420
LQISPPLHQH LNMQQHQPLT MQQPLGNQLP MQVQSALHSP TMQQGFTLQP DYQTIINPTS  480
TAAQVVTQAM EYVRSGCRNP PPQPVDWNND YCSSGGMQRD KALYLT                526

SEQ ID NO: 2          moltype = DNA  length = 4076
FEATURE               Location/Qualifiers
misc_feature          1..4076
                      note = TOX(Thymocyte Selection Associated High Mobility
                      Group Box) mRNA
source                1..4076
```

-continued

```
                      mol_type = other DNA
                      organism = synthetic construct
SEQUENCE: 2
ctcttcttct taaacaaacc acaaacggat gtgagggaag gaaggtgttt cttttactcc   60
tgagcccaga cacctcactc tgttccgtct aagcttgttt tgctgaacac tttttttaa   120
aaaaggaaaa agaaaaggag ttgcttgatg tgagagtgaa atggacgtaa gattttatcc   180
acctccagcc cagcccgccg ctgcgcccga cgctccctgt ctgggacctt ctccctgcct   240
ggacccctac tattgcaaca agtttgacgg tgagaacatg tatatgagca tgacagagcc   300
gagccaggac tatgtgccag ccagccagtc ctaccctggt ccaagcctgg aaagtgaaga   360
cttcaacatt ccaccaatta ctcctccttc cctcccagac cactcgctgg tgcacctgaa   420
tgaagttgag tctggttacc attctctgtg tcaccccatg aaccataatg gcctgctacc   480
atttcatcca caaaacatgg acctccctga aatcacagtc tccaatatgc tgggccagga   540
tggaacactg ctttctaatt ccatttctgt gatgccagat atacgaaacc cagaaggaac   600
tcagtacagt tcccatcctc agatggcagc catgagacca aggggccagc ctgcagacat   660
caggcagcag ccaggaatga tgccacatgg ccagctgact accattaacc agtcacagct   720
aagtgctcaa cttggtttga atatgggagg aagcaatgtt ccccacaact caccatctcc   780
acctggaagc aagtctgcaa ctccttcacc atccagttca gtgcatgaag atgaaggcga   840
tgatacctct aagatcaatg gtgggagaa gcggcctgcc tctgatatgg ggaaaaacc   900
aaaaactccc aaaaagaaga agaagaagga tcccaatgag ccccagaagc ctgtgtctgc   960
ctatgcgtta ttctttcgtg atactcaggc cgccatcaag ggccaaaatc caaacgctac  1020
ctttggcgaa gtctctaaaa ttgtggcttc aatgtgggac ggtttaggag aagagcaaaa  1080
acaggtctat aaaaagaaaa ccgaggctgc gaagaaggaa tacctgaagc aactcgcagc  1140
atacagagcc agccttgtat ccaagagcta cagtgaacct gttgacgtga agacatctca  1200
acctcctcag ctgatcaatt cgaagccgtc ggtgttccat gggcccagcc aggcccactc  1260
ggccctgtac ctaagttccc actatccacc acaaccggga atgaatcctc acctaactgc  1320
catgcatcct agtctcccca ggaacatagc ccccaagccg aataaccaaa tgccagtgac  1380
tgtctctata gcaaacatgg ctgtgtcccc tcctcctccc ctccagatca gcccgcctct  1440
tcaccagcat ctcaacatgc agcagcacca gccgctcacc atgcagcagc cccttgggaa  1500
ccagctcccc atgcaggtcc agtctgcctt acactcaccc accatgcagc aaggatttac  1560
tcttcaaccc gactatcaga ctattatcaa tcctacatct acagctgcac aagttgtcac  1620
ccaggcaatg gagtatgtgc gttcggggtg cagaaatcct cccccacaac cggtggactg  1680
gaataacgac tactgcagta gtgggggcat gcagagggac aaagcactgt accttacttg  1740
agaatctgaa cacctcttct ttccactgag gaattcaggg aagtgttttc accatggatt  1800
gctttgtaca gtcaaggcag ttctccattt tattagaaaa tacaagttgc taagcactta  1860
ggaccatttg agcttgtggg tcacccactc tggaagaaat agtcatgctt ctttattatt  1920
ttttttaatcc tttatggaca ttgtttttct tcttccctga aggaaatttg gaccattcag  1980
atttttatgtt ggtttttgc tgtgaagtgc tgcgctctag taactgcctt agcaactgta  2040
gatgtctcgg ataaaagtcc tggattttcc attggttttc ataatgggtg tttatatgaa  2100
actactaaag actttttaaa tggcttgatg tagcagtcat agcaagtttg taaatagcat  2160
ctatgttaca ctctcctaga gtataaaatg tgaatgtttt tgtagctaaa ttgtaattga  2220
aactggctca ttccagttta ttgatttcac aatagggggtt aaattggcaa acattcatat  2280
ttttacttca ttttttaaaac aactgactga tagttctata ttttcaaaat atttgaaaat  2340
aaaaagtatt cccaagtgat tttaatttaa aaacaaattg gcttttgtctc attgatcaga  2400
caaaaagaaa ctagtattaa gggaagcgca aacacattta ttttgtactg cagaaaaatt  2460
gcttttttgt atcacttttt gtgtaatggt tagtaaatgt catttaagtc cttttatgta  2520
taaaactgcc aaatgcttac ctggtatttt attagatgca gaaacagatt ggaaacagct  2580
aaattacaac ttttacatat ggctctgtct tattgtttct tcatactgtg tctgtattta  2640
atcttttttt atggaacctg ttgcgcctat ttatgaaata ataaatatag gtgtttgtaa  2700
gtaaatttgt tagtatttga aagaggtttc tttgatgttt taactttttgc tggcaaaaaa  2760
aaattcacgc ttggtgtgaa tactttatta tttagttttt acagtaacat gaataaagcc  2820
aaacctgctt ttcatttagc agcaaattaa agtaaccagt ccttatttct gcatttcttt  2880
ggttgatgca aacaaaaaac tattatattt aagaacttta tttcttcata cgacataaca  2940
gaattgccct ccaagtcaca caagctccaa gactaaacaa acagacaggt cctctgtctt  3000
aaaaaggtta cttcttggtt ctcagctggt tctagtcaat tctgaaccac caccccccgc  3060
ccccgcaaa aaagtaaaag tcaaaccaaa cttcctcaag ctgcatgctt ttcacaaaat  3120
ccagaaagca tttaagaatt gaactagggg ctggaagag tgaaagggaa gcatctaaaa  3180
atgaaaggtg agtaaccaga tagcaaaaga aaagggaaag ccatccaaat ttgaaagctg  3240
ttgatagaaa ttgagattct tgctgtcttt tgtgcctcta caagctacta ctcattccag  3300
aattcctggg tcttccaaga ggattcttaa ggtaccagag atttgctagg gaaccaaaag  3360
tgcttgagaa tctgcctgag ggcttgcata gctttcacat taaaaaaaga aaaagctagc  3420
agatttactc ctttttaggg gatcatatca agaaagttag tctggttgga aaccaagaga  3480
atggctgatg tctctttctt ggaatatgtg aaataaattt agcagtttaa ctaaatacaa  3540
atatatgcat tgtgtaatcc actcagaatt aaacagacaa aaggtatgct tgctttggaa  3600
tgattttagg cattgtacaa ccttgaatca cttgagcatg taataactaa taaataatgc  3660
agatccatgt gattattaaa atgactgtag ctgagagctc taattttcct gtcttgaaac  3720
tgtataagaa ctcatgtgat taagttcaca gtttattgtt tgtctgttta gtattttaga  3780
aatataccag cactactaat taactaatgt cttttattta ttatattatg ataaagtaaa  3840
aatttcactt gcattaagtc taaactgaga aggtaattac tggggaggaa atgagcagct  3900
ttgactttga caggcggttt gtgcaggaaa gcacagtgcc gtgttgttta cagctttct  3960
agagcagctg tgcgaccagg gtagagagtg ttgaaattca ataccaaata cagtaaaaac  4020
aaatgtaaat aaaagaaaac acatcatcaa taaaactgtt attatgcgtg accgta      4076
```

METHOD FOR TREATING SARS-COV-2 INFECTIOUS DISEASE

CROSS-REFERENCE TO RELATED APPLICATION(S)

This application claims priority to and the benefit of Korean Patent Application No. 10-2022-0030971 filed in the Korean Intellectual Property Office on 11 Mar. 2022, the disclosure of which is incorporated herein by reference.

INCORPORATION BY REFERENCE OF SEQUENCE LISTING

This application contains an electronic Sequence Listing submitted via the United States Patent and Trademark Office Patent Center, which is hereby incorporated by reference in its entirety for all purposes. The Sequence Listing XML file titled "NewApp_0421930003_sequenceST26.xml" was created and last modified on Mar. 9, 2023, and has a size of 8160 bytes.

BACKGROUND OF THE INVENTION

1. Field of the Invention

The present disclosure is made with the support of the Ministry of Science and ICT, Republic of Korea, under Project No. 2021R1C1 C2006896, in the research project entitled "Development of Prognosis Biomarker and Therapeutic Candidates for Post-Pandemic Diseases" in the research program named "Basic Individual Research, Sejong Science Fellowship", by the Sungkyunkwan University, under management of the National Research Foundation of Korea, from 1 Mar. 2021 to 28 Feb. 2026.

The present disclosure relates to a biomarker for diagnosis or prognostic prediction of the severity of SARS-CoV-2 infectious disease and, specifically, to a composition comprising an agent for measuring the expression level of TOX for diagnosis or prognostic prediction of the severity of SARS-CoV-2 infectious disease.

2. Description of the Prior Art

Severe acute respiratory syndrome coronavirus 2 (SARS-CoV-2) is a novel coronavirus that broke out in 2019, and the coronavirus disease-2019 (COVID-19) pandemic caused by the infection thereof is a serious threat to public health worldwide. Recent statistics indicate more than 100,000 deaths and approximately 2,000,000 confirmed cases in 180 countries around the world. The number of confirmed cases is continuously increasing, and experts predict hundreds of thousands of deaths worldwide.

Numerous research teams and global pharmaceutical companies are conducting clinical trials for SARS-CoV-2 treatment candidates. However, most of these drugs were not developed for the treatment of SARS-CoV-2 infection, but merely developed for the treatment of conventional viruses, such as Ebola virus, human immunodeficiency virus (HIV), severe acute respiratory syndrome (SARS) virus, Middle East respiratory syndrome (MERS) virus, influenza A virus (Influenza A virus), and ZIKA virus.

Various clinical studies show that COVID-19 patients have considerable difficulties in overcoming cytokine release syndrome (CRS) and severe respiratory impairment (see Med, (2020) Apr. 6 2020 and Med, 6 Apr. 2020). The US biotechnology company Genentech recently announced that the FDA has approved a Phase 3 clinical trial of Tocilizumab (Actemra) for treating hospitalized patients with severe SARS-CoV-2 pneumonia. However, even after the resolution of viral infections, the tissue damage of patients may be not completely recovered and patients may suffer serious diseases, such as acute respiratory distress syndrome (ARDS) or sepsis, which may lead to death in severe case.

The prediction of the severity of SARS-CoV-2 infectious disease is essential in establishing treatment strategies for patients, and particularly, the diagnosis of the severity of patients may be very significant for the survival of patients during the epidemic of infectious diseases when the demand for intensive care units is rapidly increasing. Hence, new biomarkers capable of quickly diagnosing SARS-CoV-2 infection and the severity thereof needs to be urgently discovered.

SUMMARY OF THE INVENTION

The present inventors, while searching and endeavoring to develop biomarkers capable of diagnosing the severity of SARS-CoV-2 infectious disease, established that the expression level of TOX protein is very closely connected with the severity of SARS-CoV-2 infectious disease, and thus completed the present disclosure.

Accordingly, an aspect of the present disclosure is to provide a composition for diagnosis or prognostic prediction of the severity of severe acute respiratory syndrome coronavirus 2 (SARS-CoV-2) infectious disease, the composition comprising an agent for measuring the protein level or mRNA expression level of thymocyte selection associated high mobility group box (TOX).

Another aspect of the present disclosure is to provide a kit for diagnosis or prognostic prediction of the severity of SARS-CoV-2 infectious disease, the kit including an agent for measuring the protein level or mRNA expression level of TOX.

Still another aspect of the present disclosure is to provide a method for providing information required for diagnosis or prognostic prediction of the severity of SARS-CoV-2 infectious disease, the method including measuring the protein level or mRNA expression level of TOX.

Still another aspect of the present disclosure is to provide a method for screening a therapeutic agent for SARS-CoV-2 infectious disease, the method including selecting a substance for reducing the protein level or mRNA expression level of TOX in a subject.

Still another aspect of the present disclosure is to provide a pharmaceutical composition for prevention or treatment of SARS-CoV-2 infectious disease, the pharmaceutical composition comprising an agent for inhibiting expression or activity of TOX protein or a polynucleotide encoding TOX protein.

Still another aspect of the present disclosure is to provide a method for treating SARS-CoV-2 infectious disease, the method including administering to a subject a composition comprising an agent for inhibiting expression or activity of TOX protein or a polynucleotide encoding TOX protein.

Still another aspect of the present disclosure is to provide a method for treating a severe SARS-CoV-2 patient, the method including: measuring the protein level or mRNA expression level of TOX in a biological sample isolated from a SARS-CoV-2 infected patient; comparing the measured protein level or mRNA expression level of TOX with that of a normal control group; and administering a composition for treatment of SARS-CoV-2 infection to a SARS-CoV-2 infected patient, from which a biological sample with a higher protein level or mRNA expression level of TOX than the normal control group is isolated.

The present inventors identified TOX, which was specifically overexpressed compared with normal subjects, in biological samples (blood) obtained from severe COVID-19 patients, and secured the same as a diagnostic marker for SARS-CoV-2 infectious disease.

More specifically, the present inventors verified that the level of TOX in the blood increased in severe COVID-19 patients. The present inventors also verified that the treatment of a septic animal model with TOX antibodies resulted in decreased survival rates and reduced levels of inflammation-related factors.

Hence, the present disclosure provides: a composition/kit for diagnosis or prognostic prediction of the severity of SARS-CoV-2 infectious disease, the composition/kit comprising an agent for measuring the protein level or mRNA expression level of thymocyte selection associated high mobility group box (TOX); a method for providing information required for diagnosis or prognostic prediction of the severity of SARS-CoV-2 infectious disease, the method including measuring the protein level or mRNA expression level of TOX; a method for screening a therapeutic agent for SARS-CoV-2 infectious disease, the method including selecting a substance for reducing the protein level or mRNA expression level of TOX in a subject; and a pharmaceutical composition for prevention or treatment of SARS-CoV-2 infectious disease, the pharmaceutical composition comprising an agent for inhibiting expression or activity of TOX protein or a polynucleotide encoding TOX protein.

Hereinafter, the present disclosure will be described in more detail.

In accordance with an aspect of the present disclosure, there is provided a composition for diagnosis or prognostic prediction of the severity of severe acute respiratory syndrome coronavirus 2 (SARS-CoV-2) infectious disease, the composition comprising an agent for measuring the protein level or mRNA expression level of thymocyte selection associated high mobility group box (TOX)

As used herein, the term "SARS-CoV-2" refers to severe acute respiratory syndrome coronavirus 2, a novel coronavirus that broke out in December 2019, and the term "COVID-1 9" refers to a respiratory infection disease caused by SARS-CoV-2 viral infection. Herein, the terms "SARS-CoV-2 infection" and "COVID-19" may be used interchangeably.

As used herein, the term "SARS-CoV-2 infectious disease" refers to a disease that is developed by SARS-CoV-2 infection and includes severe acute respiratory syndrome (SARS), acute respiratory distress syndrome (ARDS), sepsis, septic shock, pneumonia, and pulmonary edema, but is not limited thereto.

In the present disclosure, SARS-CoV-2 may cause various mutations during infection, resulting in the emergence of variants, and these variants may also fall within the SARS-CoV-2 of the present disclosure.

The term "sepsis" is a systemic inflammatory response syndrome that appears as a complication of SARS-CoV-2 infection. If the cause of sepsis is not diagnosed quickly and accurately at an early stage, the disease may progress to severe sepsis or septic shock, multiple organ dysfunction syndrome (MODS) causing even dysfunction of the lungs, kidneys, liver, and circulatory system, disseminated intravascular coagulation syndrome (DIC), acute respiratory distress syndrome, or acute renal failure, leading to death.

Therefore, the sepsis in the present disclosure encompasses sepsis related with the final stage of sepsis, severe sepsis, septic shock, and multiple organ dysfunction syndrome accompanying sepsis, disseminated intravascular coagulation syndrome, acute respiratory distress syndrome, or acute renal failure, but is not limited thereto, and includes all stages of sepsis.

As used herein, the term "diagnosis" encompasses: determining the susceptibility of a subject to a specific disease or disorder; determining whether a subject currently has a specific disease or disorder; assessing a prognosis of a subject suffering from a specific disease or disorder (e.g., identifying the status of SARS-CoV-2 infectious disease, determining the stage of SARS-CoV-2 infectious disease, or determining the therapeutic responsiveness of SARS-CoV-2 infectious disease); or therametrics (e.g., monitoring the conditions of a subject to provide information on therapeutic efficacy).

In particular, the diagnosis in the present disclosure means a diagnosis of the severity of SARS-CoV-2 infectious disease and, specifically, may mean the seriousness of a patient having SARS-CoV-2 infectious disease, specifically, the presence or absence of complications, the degree of risk of death, the presence or absence of severe acute respiratory syndrome, and the like.

The term "prognosis" in the present disclosure refers to a prediction of occurrence, progression, recovery, recurrence, and drug resistance of a disease, and indicates a prospective or preliminary evaluation. The prognosis in the present disclosure may mean the occurrence or recurrence of SARS-CoV-2 infectious disease, death caused by SARS-CoV-2 infectious disease, overall survival from SARS-CoV-2 infectious disease, or disease-free survival, but is not limited thereto.

As used herein, "expression" refers to the production of a protein or a nucleic acid. The term "protein" is used interchangeably with the term "polypeptide" or "peptide", and refers to, for example, a polymer of amino acid residues, as typically found in proteins in nature. The term "polynucleotide" or "nucleic acid" refers to single- or double-stranded deoxyribonucleotide (DNA) or ribonucleotide (RNA). Unless otherwise limited, the term includes known analogs of naturally occurring nucleotides that hybridize with nucleic acids in a manner similar to naturally occurring nucleotides. The term "mRNA" refers to an RNA molecule that carries the genetic information (gene-specific nucleotide sequence) to ribosomes that specify amino acid sequences from a specific gene during protein synthesis.

An example of the present disclosure verified that as a result of analyzing the protein level or mRNA expression level of TOX in the blood isolated from COVID-19 patients, the more severe the disease, the higher the TOX concentration. Therefore, the measurement of the protein level or mRNA expression level of TOX can lead to more accurate prediction of the severity of SARS-CoV-2 infection.

In an embodiment of the present disclosure, the agent for measuring the TOX protein level may be an antibody specifically binding to TOX protein, a fragment of the antibody, or an aptamer.

As used herein, the term "antibody" refers to an immunoglobulin that specifically binds to an antigenic site. The antibody in the present disclosure specifically binds to only TOX protein but does not react with other types of proteins than TOX. A TOX antibody may be produced by a conventional method in the art, from a protein obtained by cloning the TOX gene into an expression vector and encoded by the gene. A TOX protein-specific antibody may be produced using a fragment of TOX protein comprising a TOX antigenic site.

The form of the antibody of the present disclosure is not particularly limited, and includes a polyclonal antibody or a monoclonal antibody. A part of the whole antibody also falls within the antibody of the present disclosure as long as the part has antigen-antibody binding properties, and all types of immunoglobulin antibodies that specifically bind to TOX falls within the antibody of the present disclosure. For example, the antibody of the present disclosure may include not only a complete form of antibody with two full-length light chains and two full-length heavy chains, but also a functional fragment of the antibody molecule, that is, Fab, F(ab'), F(ab')2, and Fv, which have an antigen-binding function. Furthermore, the antibody of the present disclosure also includes special antibodies, such as humanized antibodies and chimeric antibodies, and recombinant antibodies as long such antibodies can specifically bind to TOX protein.

The TOX protein in the present disclosure preferably includes the human TOX amino acid sequence represented by SEQ ID NO: 1, and the antibody specifically binding to TOX protein in the present disclosure may be an antibody specifically binding to the protein having the amino acid sequence represented by SEQ ID NO: 1. The composition for diagnosis or prognostic prediction of the present disclosure comprising the TOX-specific antibody as an agent for measuring the expression level of TOX may further comprise an agent required for a known protein detecting method, and the TOX protein level may be measured using the present composition by employing a known protein detecting method without limitation.

As used herein, the term "aptamer" refers to single-stranded DNA (ssDNA) or RNA having high specificity and affinity for a specific material. Since aptamers have very high affinity for specific materials and are stable, can be synthesized by relatively simple methods, can be variously modified to enhance binding ability, and can target cells, proteins, and even small organic materials, the specificity and stability thereof are very high compared with antibodies that have already been developed. In the present disclosure, the type and form of aptamer are not particularly limited as long as the aptamer can bind to TOX.

In another embodiment of the present disclosure, the agent for measuring the TOX mRNA expression level may be a primer pair, probe, or combination thereof, which specifically bind to TOX mRNA.

The TOX mRNA may be derived from mammals including humans, and preferably may include the human TOX mRNA nucleotide sequence represented by SEQ ID NO: 2. The composition for diagnosis or prognostic prediction of the present disclosure comprising the TOX mRNA-specific probe or primer set as an agent for measuring the expression level of TOX may further comprise an agent required for a known RNA detecting method. The TOX mRNA level in a subject may be measured by using a known RNA detection method, without limitation, using the present composition.

As used herein, the term "primer" is a short single-stranded oligonucleotide acting as a starting point of DNS synthesis. The primer specifically binds to a polynucleotide, which is a template, using a suitable buffer under a suitable temperature, and the DNA polymerase synthesizes DNA by additionally linking a nucleoside triphosphate having a nucleotide complementary to the template DNA to the primer. The primer generally consists of a 15- to 30-sequence, and the melting temperature (Tm) at which binding to a template strand is performed varies depending on the composition and length of nucleotides.

The sequence of the primer does not need to be perfectly complementary to a sequence of some nucleotides of the template, and the primer is sufficient as long as the primer has enough complementarity within the range in which the primers can perform inherent actions thereof through the hybridization with the template. Therefore, the primer for measuring the TOX mRNA expression level in the present disclosure does not need to have a completely complementary sequence to the TOX gene sequence, and the primer is sufficient as long as the primer has a length and complementarity for the purpose of measuring the amount of TOX mRNA by amplifying a specific section of TOX mRNA or TOX cDNA through DNS synthesis. Primers for the amplification reaction consist of a set (pair) of primers that complementarily bind to a template (or sense) and an opposite side (antisense), respectively, of both ends of a specific region of the TOX mRNA to be amplified. The primers may be easily designed with reference to the nucleotide sequence of TOX mRNA or cDNA by a person skilled in the art.

In the present disclosure, the primers may be preferably one set or pair of primers, which specifically bind to TOX mRNA nucleotide sequence represented by SEQ ID NO: 2.

As used herein, the term "probe" refers to a fragment of a polynucleotide, such as RNA or DNA, capable of specifically binding to mRNA or complementary DNA (cDNA) of a specific gene and having a length of several to several hundreds of base pairs. Since the probe is labeled, the probe can be used to check for the presence or absence of target mRNA or cDNA to be bound or the expression level thereof. For the purpose of the present disclosure, a probe complementary to TOX mRNA may be used for diagnosis of infectious diseases by hybridization with a sample of a subject to measure the expression level of TOX mRNA. The selection and hybridization conditions of the probe may be selected appropriately according to the technique known in the art.

The primers or probe may be chemically synthesized using phosphoramidite solid-phase synthesis or other well-known methods. The primers or probe may be variously modified by a method known in the art within the scope within which hybridization with TOX mRNA is not impeded. Examples of such a modification are methylation, capping, substitution of at least one native nucleotide with an analogue thereof, modification between nucleotides, for example, the binding of a labeling material through an uncharged linker (e.g., methylphosphonate, phosphotriester, phosphoramidate, and carbamate) or a charged linker (e.g., phosphorothioate, and phosphorodithioate), and a fluorescence or an enzyme.

In accordance with another aspect of the present disclosure, the composition for diagnosis or prognostic prediction of the severity of SARS-CoV-2 infectious disease of the present disclosure may be applied or fabricated into a kit for diagnosis or prognostic prediction of the severity of SARS-CoV-2 infectious disease.

The kit for diagnosis or prognostic prediction of the severity of SARS-CoV-2 infectious disease of the present disclosure may further include other components or devices that are widely used in the art.

As a specific example, a kit for RT-PCR may be fabricated including primer pairs specific to the TOX gene and further including test tubes or other appropriate containers, reaction buffers, deoxynucleotides (dNTPs), enzymes such as Taq polymerase and reverse transcriptase, DNAse inhibitors, RNAse inhibitors, DEPC-water, sterile water, and the like. As another example, a kit for a DNA chip may be fabricated including essential components required for performing a DNA chip.

As still another example, a kit for ELISA may be fabricated including the antibodies specific for the protein of the gene and further including reagents capable of detecting bound antibodies, for example, labeled secondary antibodies, chromophores, enzymes, and substrates thereof. As another example, a kit for a protein chip may be fabricated including essential components required for performing a protein chip.

In addition to the kits exemplified above, various types of diagnostic kits fabricated as rapid diagnostic kits capable of detecting the gene are included.

In accordance with still another aspect of the present disclosure, there is provided a method for providing information required for diagnosis or prognostic prediction of the severity of SARS-CoV-2 infectious disease, the method including:

measuring the protein level or mRNA expression level of thymocyte selection associated high mobility group box (TOX) in a biological sample of a subject; and comparing the measured protein level or mRNA expression level of TOX with that of a normal control group.

In the present disclosure, the protein level or mRNA expression level of TOX in a biological sample is measured and the measurement result is compared with the level of a normal control group, and then if the protein or mRNA level in the sample increases, the sample may be determined to have a high severity of SARS-CoV-2 infectious disease.

After the severity of SARS-CoV-2 infectious disease is accurately determined by the method of the present disclosure, a therapeutic strategy for the patient can be established according to the severity of the disease.

The method of the present disclosure includes involving, as a subject, a mammal, particularly a human. In particular, the human subject includes a person suspected of having developed SARS-CoV-2 infectious disease, a SARS-CoV-2 infectious disease patient, or an unsuspected person who needs to be diagnosed for SARS-CoV-2 infectious disease.

As used herein, the "biological sample" may be used without limitation as long as it is collected from a subject to be diagnosed for SARS-CoV-2 infectious disease or to be predicted for the therapeutic response of the disease, and examples of the biological sample may include cells or tissues obtained by biopsy, blood, whole blood, serum, plasma, saliva, cerebrospinal fluid, various secretions, urine, feces, and the like. The sample may be pre-treated before use for detection or diagnosis. For example, examples of the pre-treatment may include homogenization, filtration, distillation, extraction, concentration, inactivation of interference components, reagent addition, and the like.

In the present disclosure, the term "measuring protein level" refers to a process, in which the presence or absence and expression level of the protein expressed from the TOX gene of the present disclosure are checked in a biological sample to examine the progress of SARS-CoV-2 infectious, and is performed by measuring the amount of the protein. The protein level of TOX may be detected or measured using an antibody specifically binding to TOX protein. The TOX protein-specific antibody is as described in the composition for diagnosis or prognostic prediction of the present disclosure.

For the measurement of the protein level of TOX, methods known in the art may be used without limitation, and examples thereof may include Western blotting, dot blotting, enzyme-linked immunosorbent assay (ELISA), radioimmunoassay (RIA), radioimmunodiffusion, Ouchterlony immunodiffusion, rocket immunoelectrophoresis, immunohistostaining, immunoprecipitation assay, complement fixation assay, flow cytometry (FACS), protein chip assay, or the like, but are not limited thereto.

In the present disclosure, the term "measuring mRNA expression level" refers to a process, in which the presence or absence and expression level of TOX mRNA of the present disclosure are checked in a biological sample to examine the progress of SARS-CoV-2 infectious, and is performed by measuring the amount of mRNA. Regarding the mRNA level of TOX, the presence and expression level of TOX mRNA in a biological sample may be measured by using a primer set or probe specifically binding to TOX mRNA to amplify TOX mRNA or cDNA from the biological sample or by using hybridization with a probe. The primers and probe for TOX are as described in the composition for diagnosis or prognostic prediction of the present disclosure.

For the measurement of the mRNA expression level of TOX, conventional expression level determining methods known in the art may be used without limitation, and examples thereof may include reverse transcription polymerase chain reaction (RT-PCR), competitive RT-PCR, real-time RT-PCR, RNase protection assay (RPA), northern blotting, DNA microarray chip, RNA sequencing, hybridization using nano-string, in situ hybridization of tissue sections, and the like, but are not limited thereto.

As used herein, the term "detection" includes quantitative and/or qualitative analysis and encompasses detecting the presence or absence and detecting expression levels. Such methods are known in the art, and a person skilled in the art could select an appropriate method to implement the present disclosure.

As used herein, the term "increase in level" means that a previously undetected one is detected or the amount of detection is relatively increased compared with a normal level. It can be understood by a person skilled in the art that the meaning of the term opposite thereto has an opposite meaning on the basis of the definition. In the present disclosure, the "increases" in the level may mean a 1- to 1.5-fold, 1.5-to 2-fold, 2- to 2.5-fold, 2.5- to 3-fold, 3- to 3.5-fold, 3.5- to 4-fold, 4- to 4.5-fold, 4.5- to 5-fold, to 5.5-fold, 5.5- to 6-fold, 6- to 6.5-fold, 6.5- to 7-fold, 7- to 7.5-fold, 7.5- to 8-fold, 8- to 8.5-fold, 8.5- to 9-fold, 9- to 9.5-fold, 9.5- to 10-fold, or at least 10-fold increase, but is not limited thereto.

In the present disclosure, the "reduction" in the level may mean a 1- to 1.5-fold, 1.5-to 2-fold, 2- to 2.5-fold, 2.5- to 3-fold, 3- to 3.5-fold, 3.5- to 4-fold, 4- to 4.5-fold, 4.5- to 5-fold, to 5.5-fold, 5.5- to 6-fold, 6- to 6.5-fold, 6.5- to 7-fold, 7- to 7.5-fold, 7.5- to 8-fold, 8- to 8.5-fold, 8.5- to 9-fold, 9- to 9.5-fold, 9.5- to 10-fold, or at least 10-fold reduction, but is not limited thereto.

When the protein level or mRNA expression level of TOX in a subject measured by the method is compared with the protein level or mRNA expression level of TOX in a control group measured by the same method, an increase in the protein level or mRNA expression level of TOX may indicate that the subject has developed SARS-CoV-2 infectious disease or is predicted to have a poor prognosis of the SARS-CoV-2 infectious disease. In particular, the term "predicted to have a poor prognosis" may mean the prediction of having a high probability of developing SARS-CoV-2 infectious disease, severe symptoms of SARS-CoV-2 infectious disease, a high probability of death from SARS- CoV-2 infectious disease, or a high probability of recurrence of SARS-CoV-2 infectious disease.

In the present disclosure, a normal control may be a biological sample isolated from a normal person who has never been diagnosed with a SARS-CoV-2 infectious disease.

In accordance with still another aspect of the present disclosure, there is provided a method for screening a therapeutic agent for SARS-CoV-2 infectious disease, the method including selecting a substance for reducing the protein level or mRNA expression level of thymocyte selection associated high mobility group box (TOX) in a subject.

In the present disclosure, when the protein level or mRNA expression level of TOX in a subject is measured and then the administration of a candidate substance for treatment of SARS-CoV-2 infectious disease shows a reduction in the protein level or mRNA expression level compared with the previously level, the candidate substance can be used as a therapeutic agent for SARS-CoV-2 infectious disease.

As used herein, the term "candidate substance" refers to an unknown substance that is used to examine whether or not it affects the activity of TOX protein in a biological sample. Examples of the candidate substance include small interference RNA (siRNA), short hairpin RNA (shRNA), microRNA (miRNA), ribozyme, DNAzyme, peptide nucleic acids (PNA), antisense oligonucleotide, recombinant plasmid, nanoparticles, proteins, oligopeptides, antibodies, aptamers, native extracts or chemicals, but are not limited thereto.

In accordance with still another aspect of the present disclosure, there is provided a pharmaceutical composition for prevention or treatment of SARS-CoV-2 infectious disease, the pharmaceutical composition comprising an agent for inhibiting expression or activity of thymocyte selection associated high mobility group box (TOX) or a polynucleotide encoding TOX protein.

As used herein, the term "prevention" refers to any action that inhibits or delays the development of SARS-CoV-2 infectious disease by administration of the composition of the present disclosure.

As used herein, the "treatment" refers to any action that alleviates or advantageously changes symptoms of SARS-CoV-2 infectious disease by administration of the composition of the present disclosure.

In the present disclosure, the agent for inhibiting expression or activity of TOX protein or a polynucleotide encoding TOX protein may be an antibody specifically binding to TOX or an antigen-binding fragment thereof, but is not limited thereto.

As used herein, the term "antigen-binding fragment" refers to a fragment that retains an antigen-binding function, and encompasses (Fab), F(ab'), F(ab')$_2$, and chemically linked F(ab')$_2$, Fv, and the like. Of the antibody fragments, Fab has a structure composed of light chain and heavy chain variable domains, a light chain constant domain, and the heavy chain first constant domain (CH1), with one antigen-binding site. Fab' is different from Fab in that the former has a hinge region comprising at least one cysteine residue at the C-terminus of the heavy chain CH1 domain. F(ab')$_2$ antibody is generated by a disulfide bond formed between cysteine residues of the high regions of Fab' fragments. Fv is a minimal antibody segment having only a heavy chain variable domain and a light chain variable domain, and recombinant techniques for producing Fv fragments are disclosed in WO 88/10649, WO 88/106630, WO 88/07085, WO 88/07086, and WO 88/09344. Two-chain Fv is a fragment in which a heavy chain variable domain and a light chain variable domain are linked by a non-covalent bond, and single-chain Fv is a fragment in which a heavy chain variable domain and a light chain variable domain are generally linked by a covalent bond via a peptide linker or are directly linked at the C-terminal, forming a dimer-like structure, like the two-chain Fv. These antibody fragments may be obtained using proteolytic enzymes (e.g., Fab fragments may be obtained by restriction-cleaving the whole antibody with papain, and F(ab')$_2$ fragments may be obtained by cleaving the whole antibody with pepsin), or may be fabricated by genetic recombinant techniques.

The pharmaceutical composition according to the present disclosure may comprise a pharmaceutically acceptable carrier, in addition to the active ingredient. Examples of the pharmaceutically acceptable carrier comprised in the pharmaceutical composition according to the present disclosure may include saline, buffered saline, water, glycerol, polyethylene glycol, vegetable oils, isopropyl myristate, and ethanol.

When the pharmaceutical composition of the present disclosure is formulated into a preparation, the preparation may be formulated using ordinarily used diluent or vehicles, such as a filler, an extender, a binder, a wetting agent, a disintegrant, or a surfactant.

Examples of solid preparations for oral administration include a tablet, pills, a powder, granules, a capsule, a troche, and the like, and such solid preparations may be prepared by mixing at least one peptide according to the present disclosure with at least one vehicle, such as starch, calcium carbonate, sucrose, lactose, or a gelatin. In addition to simple vehicles, lubricants such as magnesium stearate and talc may also be used. Examples of liquid preparations for oral administration correspond to a suspension, an oral liquid, an emulsion, a syrup, and the like. In addition to commonly used simple diluents, such as water and liquid paraffin, various vehicles, such as a wetting agent, a sweetener, an aroma, and a preservative, may be included in the liquid preparation. Examples of preparations for parenteral administration include a sterilized aqueous solution, a non-aqueous solvent, a suspension solvent, an emulsion, a freeze-drying agent, a suppository, and the like.

Examples of the non-aqueous solvent and the suspension solvent may include propylene glycol, polyethylene glycol, a vegetable oil such as an olive oil, an injectable ester such as ethylolate, and the like. Examples of a substrate for the suppository may include Witepsol, Macrogol, twin 61, cacao butter, laurin butter, glycerol, gelatin, and the like.

The composition of the present disclosure may be administered orally or parenterally (e. g, intravenous, subcutaneous, intraperitoneal, or topical application) according to a desired method, and the dose of the composition depends on the condition and body weight of a patient, severity of disease, drug form, and route and time of administration, but may be appropriately selected by a person skilled in the art.

The composition according to the present disclosure is administered at a pharmaceutically effective amount. As used herein, the term "pharmaceutically effective amount" refers to an amount sufficient to treat a disease at a reasonable benefit/risk ratio applicable to medical treatment, and the level of effective dose may be determined according to the factors including the type and severity of a disease of a patient, activity of a drug, sensitivity to a drug, time of administration, route of administration, and rate of excretion, duration of treatment, and drugs used in combination, and other factors that are well known in the field of medicine.

The composition according to the present disclosure may be administered as an individual therapeutic agent or administered in combination with another therapeutic agent, and may be administered sequentially or simultaneously with a conventional therapeutic agent, and may be administered in either single or multiple doses. It is important that the composition is administered at an amount at which a maximum effect can be obtained with a minimum amount that does not cause side effects considering all of the above factors, and the amount can be easily determined by a person skilled in the art.

Specifically, the effective amount of the composition of the present disclosure may vary depending on the age, sex, condition, and body weight of a patient. In general, 0.001-150 mg, preferably 0.01-100 mg per 1 kg of the body weight may be administered daily or every other day, or divided into one to three times a day. However, the amount of the composition may be increased or decreased according to the route of administration, the severity of obesity, patient's sex, weight and age, and the like, and thus in no way limits the scope of the present disclosure.

In accordance with still another aspect of the present disclosure, there is provided a method for treating SARS-CoV-2 infectious disease, the method including administering to a subject the above-described pharmaceutical composition.

As used herein, the "subject" refers to an object in need of treatment of a disease, and more specifically, refers to a mammal, such as a human or non-human primate, a mouse, a rat, a dog, a cat, a horse, or a cow.

As used herein, the "administration" refers to providing a subject with a predetermined composition of the present disclosure by any appropriate method.

As used herein, the term "treatment" means any action that alleviates or beneficially changes a target disease and the accompanying abnormal metabolic symptoms by the administration of the pharmaceutical composition according to the present disclosure, and the term "alleviation" refers to any action that reduces parameters associated with a disease, for example, severity of a symptom by the administration of the composition of the present disclosure.

In an embodiment of the present disclosure, the agent for inhibiting expression or activity of TOX protein or a polynucleotide encoding TOX protein may be an antibody or an antigen-binding fragment thereof, a small-molecule compound, siRNA, shRNA, miRNA, or a combination thereof.

In the present disclosure, the "small-molecule compound" may be obtained using a standard method known to a person skilled in the art. Such a method includes chemical organic synthesis or biological means. The biological means include purification from a biological source, recombinant synthesis, and in vitro translation systems, using methods well known in the art. The small molecule compound of the present disclosure may include an organic molecule, an inorganic molecule, a biomolecule, a synthetic molecule, and the like.

Combinatorial libraries of molecularly diverse chemical compounds potentially useful in treating a variety of diseases and conditions are well known in the art as are method of making the libraries. The method may use a variety of techniques well-known to a person skilled in the art including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

As used herein, "siRNA" is a short double-stranded RNA (dsRNA) that mediates efficient gene silencing in a sequence-specific manner. The siRNA of the present disclosure is used to decrease the protein level of TOX. RNA interference (RNAD is a phenomenon in which the introduction of double-stranded RNA (dsRNA) into a diverse range of organisms and cell types causes degradation of the complementary mRNA. In cells, long dsRNAs are cleaved into short 21-25 nucleotide small interfering RNAs, or siRNAs, by a ribonuclease known as Dicer. The siRNA subsequently assembles with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. For example, literatures [U.S. Pat. No. 6,506,559; Fire et al., 1998, Nature 391(19):306-311; Timmons et al., 1998, Nature 395:854; Montgomery et al., 1998, TIG 14(7):255-258; Engelke, Ed., RNA Interference (RNAi) Nuts & Bolts of RNAi Technology, DNA Press, Eagleville, PA (2003); and Hannon, Ed., RNAi A Guide to Gene Silencing, Cold Spring Harbor Laboratory Press, Cold Spring Harbor, NY (2003). Soutschek et al. (2004, Nature 432:173-178)] describes a chemical modification to siRNA that aids in intravenous systemic delivery. Optimizing siRNA involves the consideration of overall G/C content, CIT content at the termini, Tm and the nucleotide content of the 3' overhang. See, for instance, [Schwartz et al., 2003, Cell, 115:199-208 and Khvorova et al., 2003, Cell 115:209-216]. Therefore, the present disclosure also includes a method for decreasing the level of TOX by using RNAi techniques.

The present disclosure provides a vector including an siRNA or antisense polynucleotide. In another embodiment, the siRNA or antisense polynucleotide inhibits the expression of TOX. The incorporation of a desired polynucleotide into a vector and the choice of vectors is well-known in the art.

The expression vectors described herein encode a short hairpin RNA (shRNA) inhibitor. shRNA inhibitors are well known in the art and are directed against the mRNA of a target, thereby decreasing the expression of the target. The encoded shRNA is expressed by a cell, and is then processed into siRNA. For example, in certain instances, the cell possesses native enzymes (e.g., dicer) that cleaves the shRNA to form siRNA.

The siRNA, shRNA, or antisense polynucleotide can be cloned into a number of types of vectors as described elsewhere herein. For expression of the siRNA or antisense polynucleotide, at least one module in each promoter functions to position the start site for RNA synthesis.

In order to assess the expression of the siRNA, shRNA, or antisense polynucleotide, an expression vector to be introduced into a cell can also comprise either a selectable marker gene or a reporter gene or both thereof to facilitate identification and selection of expressing cells from the population of cells sought to be transfected or infected using a viral vector. The selectable marker may be carried on a separate piece of DNA and used in a co-transfection procedure.

Both selectable markers and reporter genes may be flanked with appropriate regulatory sequences to enable expression in the host cells. Useful selectable markers are known in the art and include, for example, antibiotic-resistance genes, such as neomycin resistance and the like.

In accordance with still another aspect of the present disclosure, there is provided a method for treating a severe SARS-CoV-2 patient, the method including: measuring the protein level or mRNA expression level of TOX in a biological sample isolated from a SARS-CoV-2 infected patient; comparing the measured protein level or mRNA expression level of TOX with that of a normal control group; and administering a composition for treatment of SARS-CoV-2 infection to a SARS-CoV-2 infected patient, from which a biological sample with a higher protein level or mRNA expression level of TOX than the normal control group is isolated.

The composition for treatment of SARS-CoV-2 infection may comprise remdesivir, regdanvimab, ritonavir-boosted nirmatrelvir, molnupiravir, dexamethasone, hydrocortisone, prednisolone, methylprednisolone, tocilizumab, baricitinib, convalescent plasma, casirivimab, imdevimab, sotrovimab, bamlanivimab, etesevimab, or a combination thereof.

The biological sample may be at least one selected from the group consisting of blood, plasma, serum, saliva, nasal mucus, sputum, capsular fluid, amniotic fluid, ascites, cervical or vaginal discharge, urine, and cerebrospinal fluid.

The present disclosure provides a composition for diagnosis of SARS-CoV-2 infectious disease, a diagnostic kit, a method for providing information for diagnosis, a method for screening a therapeutic agent, and a composition for prevention or treatment. According to the present disclosure, it is expected that the diagnosis or prognostic prediction of the severity of SARS-CoV-2 infectious disease can be attained, and the control of expression and activity of TOX, which is a marker of the present disclosure, can be advantageously used in the development of a therapeutic agent for SARS-CoV-2 infectious disease.

DETAILED DESCRIPTION OF THE EXEMPLARY EMBODIMENTS

Figure 1:
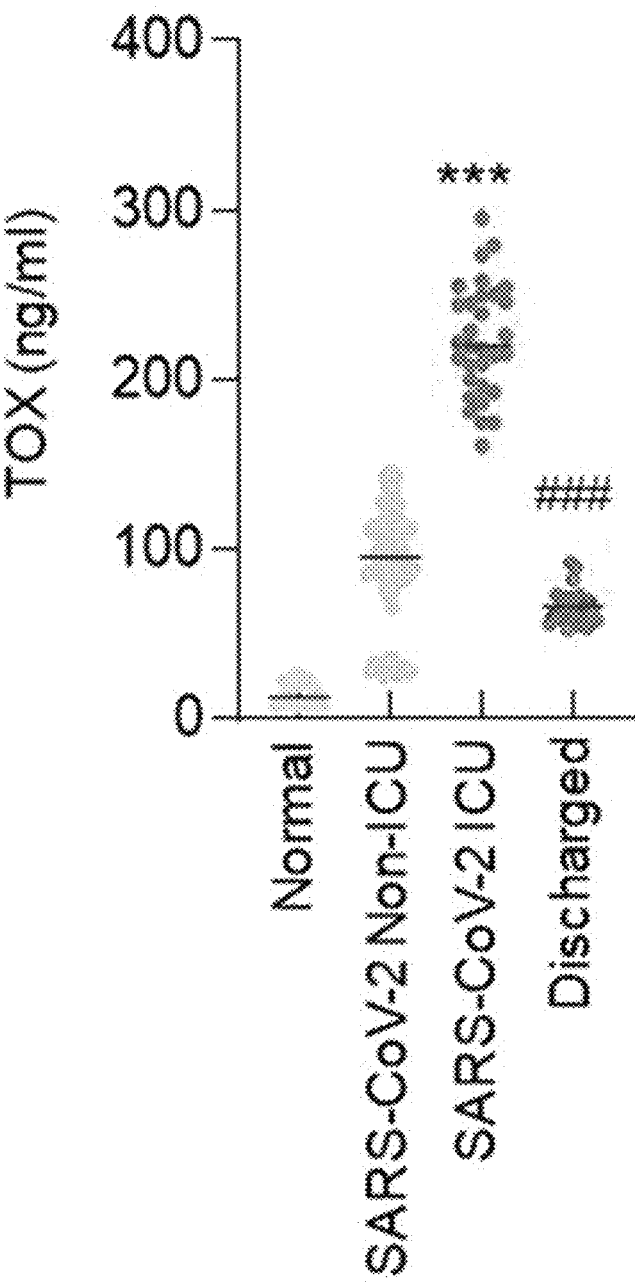
FIG. 1 shows the results of measuring the concentration of TOX in the blood of COVID-19 patients according to an example of the present disclosure (***p<0.001).

Hereinafter, the present disclosure will be described in more detail with reference to exemplary embodiments. These exemplary embodiments are provided only for the purpose of illustrating the present disclosure in more detail, and therefore, according to the purpose of the present disclosure, it would be apparent to a person skilled in the art that these examples are not construed to limit the scope of the present disclosure.

Preparative Example: Preparation of Plasma Samples

After patient information and blood samples were secured from SARS-CoV-2 (COVID-19) infected patients, the blood was analyzed. Specifically, 85 mild COVID-19 (Non-ICU) patients, 31 severe COVID-19 (ICU) patients, 31 COVID-19 (Discharged) patients discharged after hospitalization, and 20 normal controls were participated, and with respect to mild/severe COVID-19, "severe" patients were defined as patients who have received a respiratory intensive care in the intensive care unit (ICU) due to acute respiratory distress syndrome (ARDS) or sepsis, according to the ICU admission history. Plasma samples were prepared by centrifugation within 48 hours of whole blood collection at 2000 xg for 5 minutes. The study protocol was approved by the clinical trial Institutional Review Board of Yeungnam University Hospital in Daegu (IRB Nos. 2018-05-022, 2020-03-057, and 2020-05-031-001), and informed consent was obtained from all the patients.

Example 1: Discovery of TOX as Biomarker for SARS-CoV-2 Infection

To determine the influence of SARS-CoV-2 infection on cellular and molecular changes, first, the blood of patients with various COVID-19 severities (mild COVID-19 patients, severe COVID-19 patients, and COVID-19 patients discharged after hospitalization) was analyzed.

TABLE 1

| Comparison of laboratory findings of patients with SARS-CoV-2 infection | | | | |
|---|---|---|---|---|
| Classification | SARS-CoV-2 Non-ICU (n = 85) | SARS-CoV-2 ICU (n = 31) | Discharged (n = 31) | P-value |
| White blood cell count, ×10⁹/L | 6.1 ± 3.2 | 8.9 ± 3.3 | 5.6 ± 1.1 | 0.001 |

TABLE 1-continued

| | Comparison of laboratory findings of patients with SARS-CoV-2 infection | | | |
|---|---|---|---|---|
| Classification | SARS-CoV-2 Non-ICU (n = 85) | SARS-CoV-2 ICU (n = 31) | Discharged (n = 31) | P-value |
| Neutrophil count, ×10⁹/L | 4.1 ± 3.2 | 7.7 ± 3.3 | 3.0 ± 0.9 | <0.001 |
| Lymphocyte count, ×10⁹/L | 1.5 ± 0.7 | 0.8 ± 0.3 | 1.9 ± 0.5 | <0.001 |
| Hemoglobin, g/dL | 13.0 ± 1.6 | 13.5 ± 1.7 | 12.6 ± 1.5 | 0.143 |
| Platelets, ×10⁹/L | 245.0 ± 107.9 | 186.7 ± 64.9 | 258.6 ± 75.0 | 0.069 |
| Albumin, g/dL | 3.9 ± 0.5 | 3.0 ± 0.3 | 4.0 ± 0.4 | <0.001 |
| Alanine aminotransferase, IU/L | 30.1 ± 26.3 | 58.8 ± 93.6 | 38.8 ± 26.1 | 0.033 |
| Aspartate aminotransferase, IU | 37.5 ± 26.6 | 100.3 ± 97.0 | 28.4 ± 9.3 | <0.001 |
| Total bilirubin, mg/dL | 0.8 ± 0.4 | 1.1 ± 0.6 | 1.4 ± 4.3 | 0.398 |
| Blood urea nitrogen, mg/dL | 14.6 ± 9.0 | 20.0 ± 11.4 | 10.8 ± 3.1 | 0.001 |
| Creatinine, mg/dL | 0.8 ± 0.5 | 1.0 ± 0.3 | 0.7 ± 0.2 | 0.107 |
| Creatinine phosphokinase, IU/L | 100.7 ± 159.1 | 131.9 ± 122.0 | 71.1 ± 68.3 | 0.332 |
| Lactate dehydrogenase, IU/L | 555.5 ± 184.0 | 1272.6 ± 542.1 | 380.4 ± 131.8 | <0.001 |
| C-reactive protein, mg/dL | 4.2 ± 6.7 | 17.7 ± 9.5 | 0.4 ± 1.1 | <0.001 |

Data are presented as mean ± standard error of the mean. (one-way ANOVA).

As above, it was discovered during the finding of bio-markers for SARS-CoV-2 infection that the transcription factor TOX was present in the serum of COVID-19 patients, and additional experiments were conducted on TOX as follows.

Example 2: Levels of TOX in SARS-CoV-2 Infected Patients

ELISA

Recombinant TOX protein (Abcam, ab160644) was diluted to 1 µg/100 µL, coated on Nunc-Immuno™ MicroWell™ 96-well plates, and incubated overnight at 4° C. Prior to use, the plates were washed 3 times with PBST and blocked with 3% BSA in PBS at 37° C. for 30 minutes. Primary antibody (TOX antibody, Cell signaling Technology, #99036) (1:2000 dilution) and SARS-CoV-2 infected patient plasma sample (20 µg) were pre-incubated at 37° C. for 1 hour, and then the cultured sample was transferred to a peptide-coated plate and incubated at 37° C. for 1 hour. The plates were washed 5 times with PBST, incubated with secondary antibody (Cell signaling Technology, #7074) (1:5000 dilution) at 37° C. for 30 minutes, and then washed 5 times with PBST. The washed plates were treated with a 100 µL/well TMB ELISA substrate for 10 minutes at 37° C. and then a 100 µL/well stop solution was added. The detection was performed at 450 nm with an ELISA plate reader (Tecan, Austria).

PBMC Separation

Peripheral blood mononuclear cells (PBMCs) were separated by a Percoll density gradient (pH 8.5-9.5, Sigma-Aldrich, UK) with reference to Blood. 2014 Jan. 9; 123(2): 239-48. The separated PBMCs were suspended in RPMI 1640 medium (Sigma-Aldrich). A purity of 95% and a cell viability of 97% were confirmed by trypan blue staining.

Real-Time PCR

Herein, 1 µg of total RNA was reverse transcribed into random hexamers by using expand reverse transcriptase (Roche) to generate cDNA in PBMCs. Real-time PCR was performed using the LightCycler FastStart DNA Master SYBR Green I by Roche Diagnostics GmbH, according to the manufacturer's protocol: 95° C. for 10 min (initial denaturation), 95° C. for 10 min (denaturation), 60° C. for 5 min (annealing), and 72° C. for 15 min (elongation), 45 cycles. The mRNA expression levels were determined according to the gene-specific standard curve.

Time-Course Analysis

While the separated PBMCs were incubated for 24 hours, the level of TOX secretion was analyzed by TOX ELISA, and the cell viability was analyzed by WST-1 reagent.

Computed Tomography

Lung tissues of SARS-CoV-2 patients were examined using computed tomography (CT) imaging.

Figure 2:
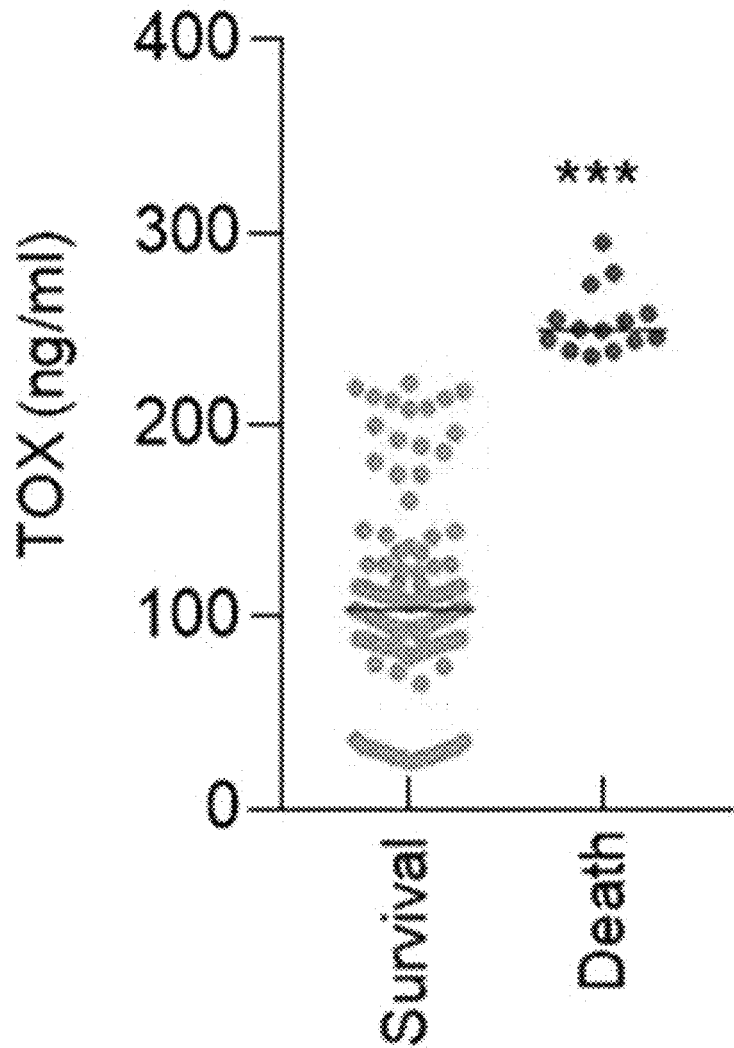
FIG. 2 shows the results of measuring the concentration of TOX in the blood of COVID-19 patients by fatality (survival or death) according to an example of the present disclosure (***p<0.001).

As a result, as shown in FIG. 1, the TOX protein level was significantly increased in the blood of the severe COVID-19 patients (SARS-CoV-2 ICU). In particular, the TOX protein level was again decreased in the discharged patients. In addition, as shown in FIG. 2, the TOX level was maintained low in the plasma of surviving patients (Survival), while a high level of TOX was still observed in the dead patients (Death).

Figure 3:
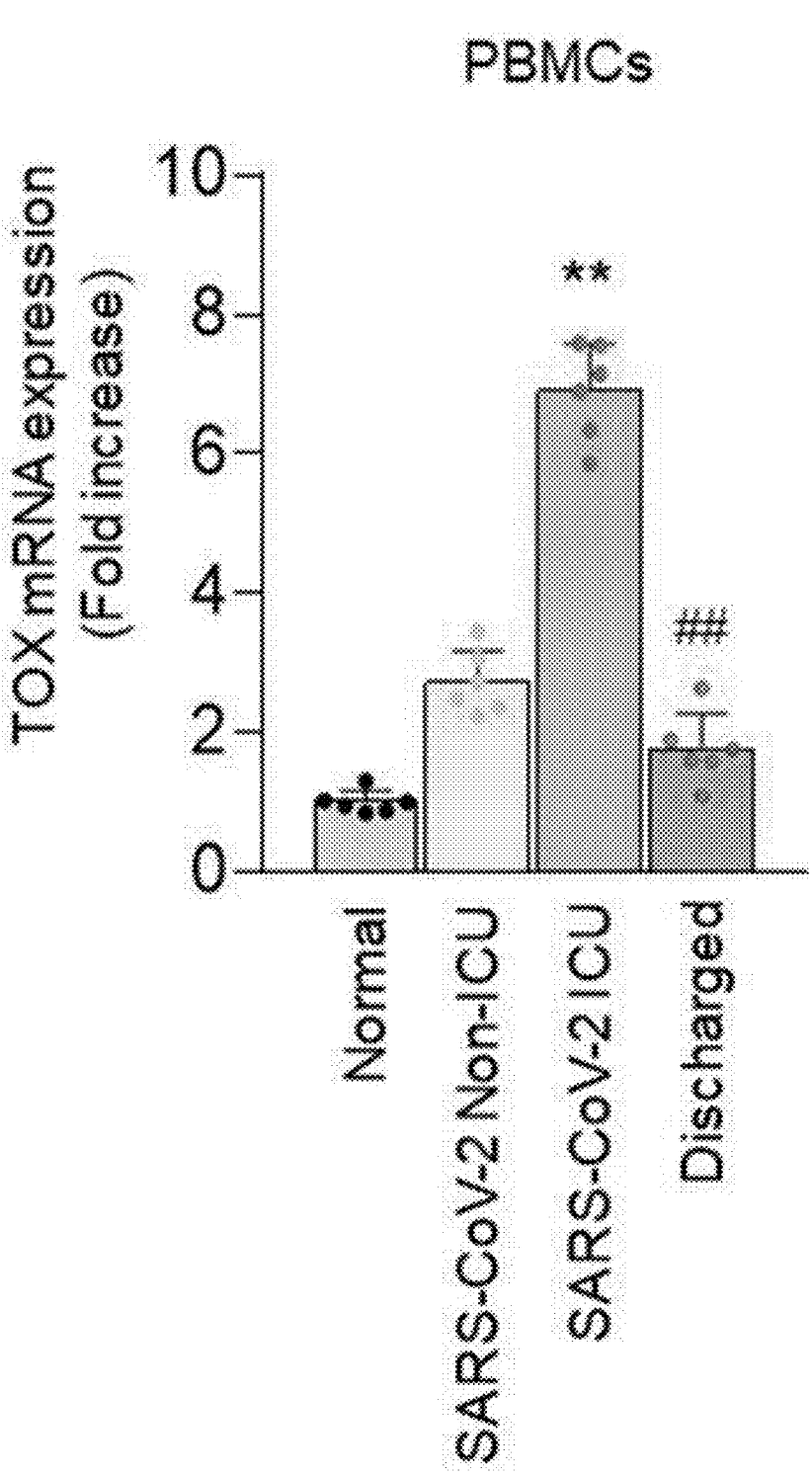
FIG. 3 shows the results of measuring the TOX mRNA expression level in PBMCs separated from the blood of COVID-19 patients according to an example of the present disclosure (*p<0.01, ##p<0.01).
Figure 4:
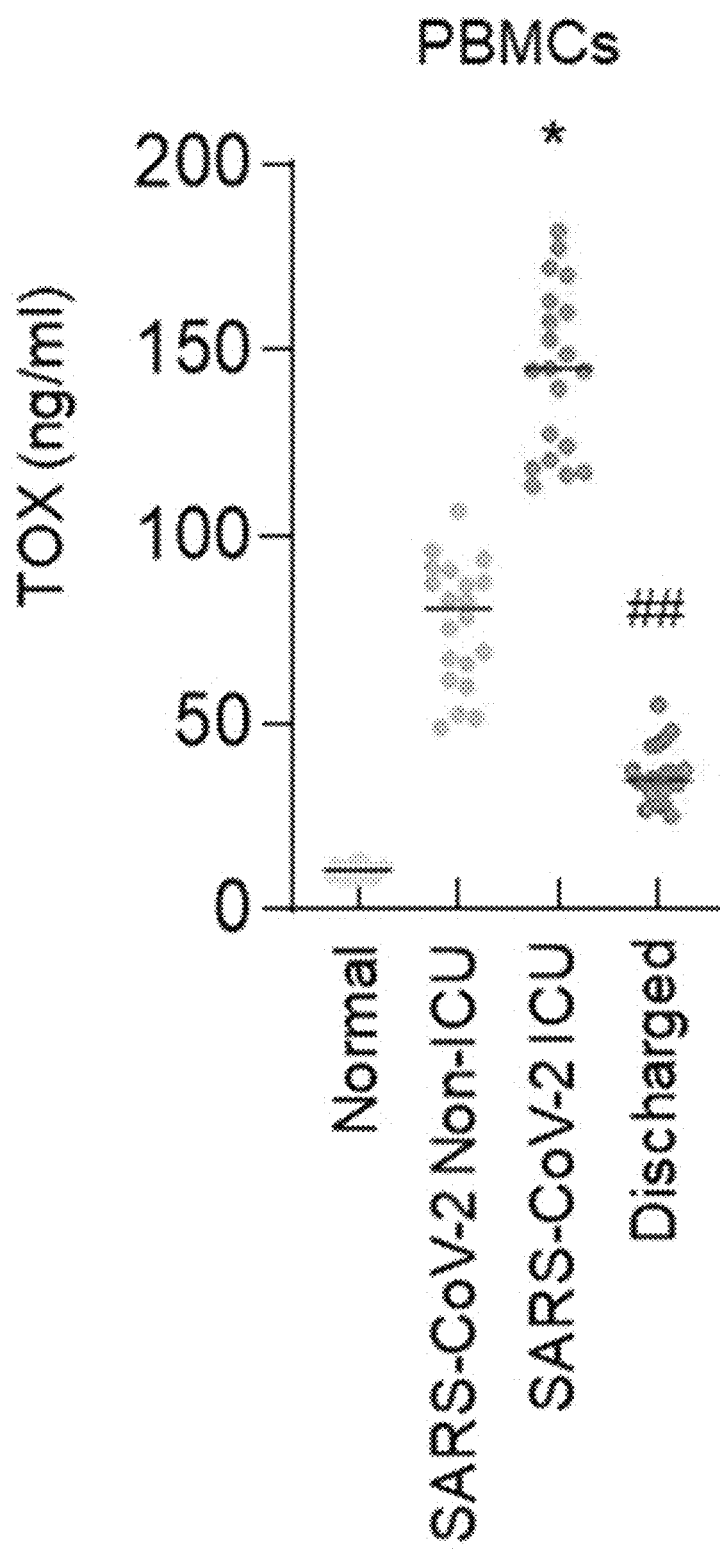
FIG. 4 shows the results of measuring the amount of TOX protein secreted in PBMCs separated from the blood of COVID-19 patients according to an example of the present disclosure (*p<0.05, ##p<0.01).
Figure 5:
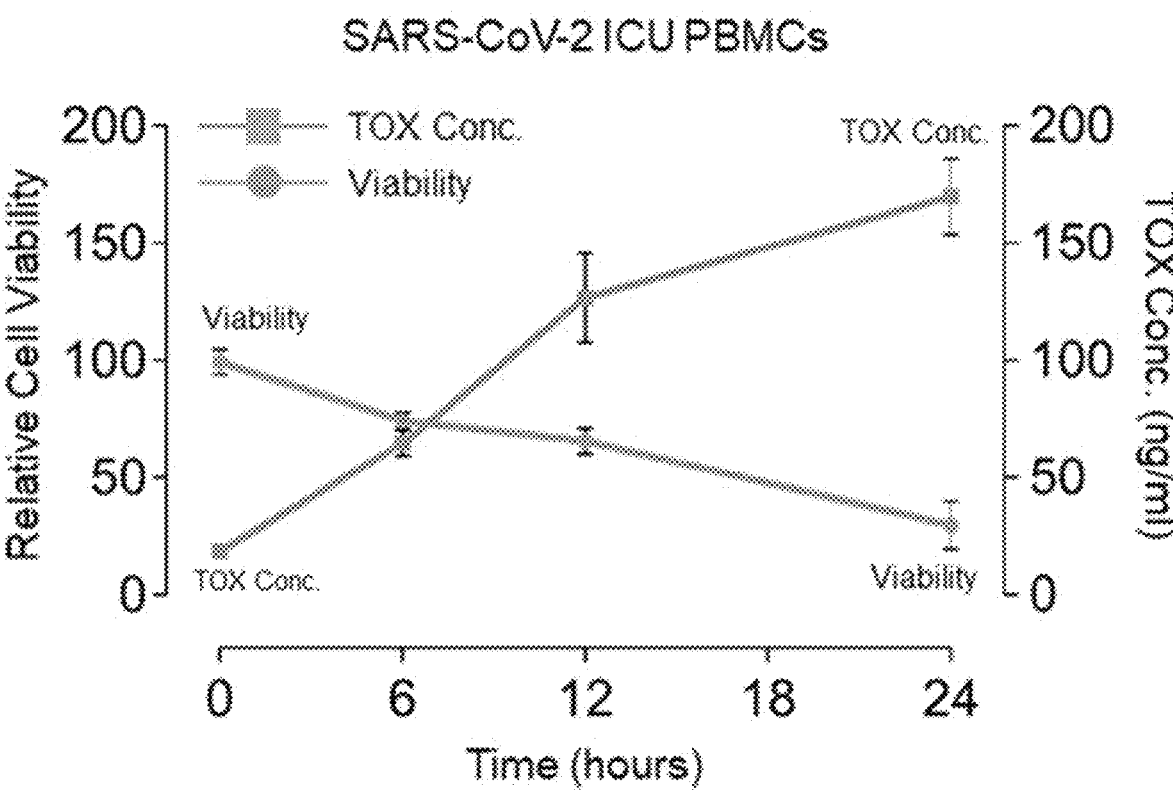
FIG. 5 shows the results of examining the cell viability and TOX secretion over time in PBMCs separated from the blood of COVID-19 patients according to an example of the present disclosure.

Furthermore, as shown in FIG. 3, the TOX mRNA expression level was significantly increased in PBMCs separated from the blood of the severe COVID-19 patients (SARS-CoV-2 ICU). Similarly, the TOX mRNA expression level was again decreased in the discharged patients. As shown in FIG. 4, the TOX protein level was also significantly increased in PBMCs separated from the blood of the severe COVID-19 patients (SARS-CoV-2 ICU). Similarly, the TOX protein level was again decreased in the discharged patients. Furthermore, as shown in FIG. 5, the cell viability was reduced as the TOX level was increased in PBMCs separated from the blood of the severe COVID-19 patients (SARS-CoV-2 ICU).

Figure 6:
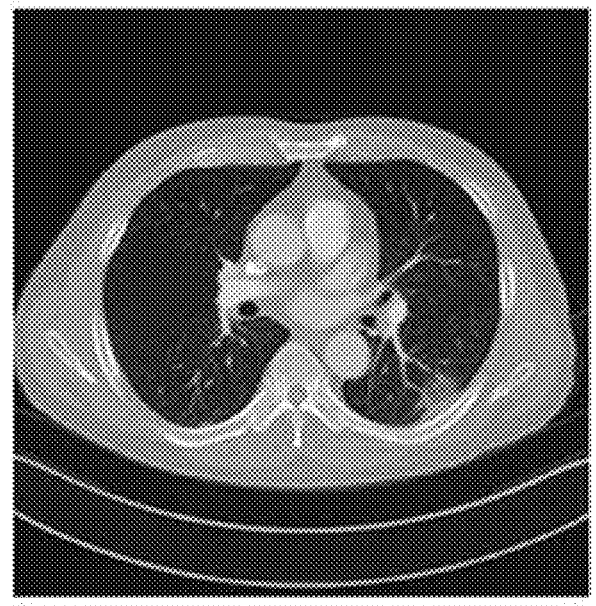
FIG. 6 shows the results of comparing CT images of lung depending on the expression difference in the concentration of TOX in the blood in the mild COVID-19 patient and severe COVID-19 patient according to an example of the present disclosure.
Figure 6:
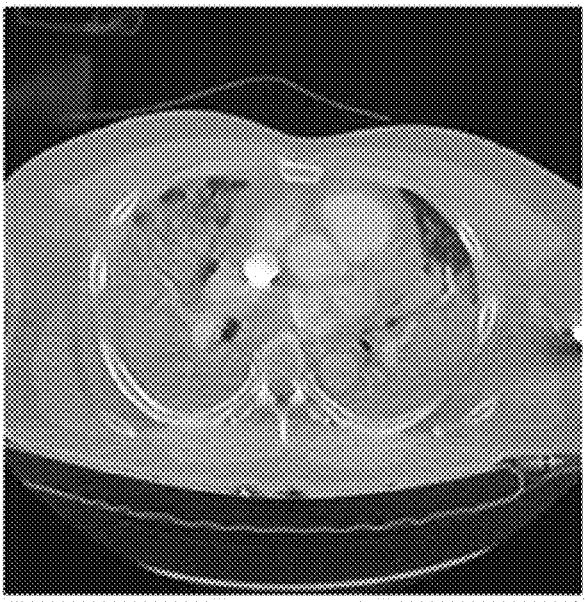

Last, as shown in FIG. 6, the COVID-19 patients with a high TOX level in the plasma suffered severe lung damage compared with the patients with a low TOX level.

These results indicate a correlation between the TOX protein level and the severity of COVID-19 disease.

17

18

Example 3: Effect of TOX on Inflammation of SARS-CoV-2 Infected Patients

PBMCs isolated from the patients with SARS-CoV-2 infectious disease in Example 2 were cultured with recombinant TOX protein at 37° C. for 24 hours. The supernatant was used for cytokine ELISA analysis, and the lysate was used for NF-κB activity assay. All experiments were independently performed at least three times.

Cytokine ELISA

The cytokine concentrations in the plasma were quantified using commercially available ELISA kits according to the manufacturers instructions, and detected at 450 nm with an ELISA plate reader (Tecan). The kits used were as follows: Human IL-1β Quantikine ELISA kit (DLB50, R&D Systems, USA), Human IL-4 Quantikine ELISA kit (D4050, R&D Systems), Human IL-6 Quantikine ELISA kit (D6050, R&D Systems), Human IL-10 Quantikine ELISA Kit (D1000B, R&D Systems), Human IFN-γ Quantikine ELISA Kit (DIF50, R&D Systems), and Human TNF-α Quantikine ELISA kit (DTAOOD, R&D Systems).

NF-κB Activity Kit

NF-κB activity was analyzed using an ELISA-based NF-κB family transcription factor assay kit (43296; Active Motif, USA). Specifically, a nuclear extract (2 μg) was incubated in 96-well plates, on which NF-κB consensus oligonucleotides were immobilized, at 37° C. for 1 hour. The captured complex was incubated with NF-κB primary antibody at 37° C. for 1 hour and then incubated with HRP-conjugated secondary antibody at 37° C. for 1 hour. The antibodies were detected by determining the optical density (OD) at 450 nm through a Tecan Spark microplate reader.

Figure 7:
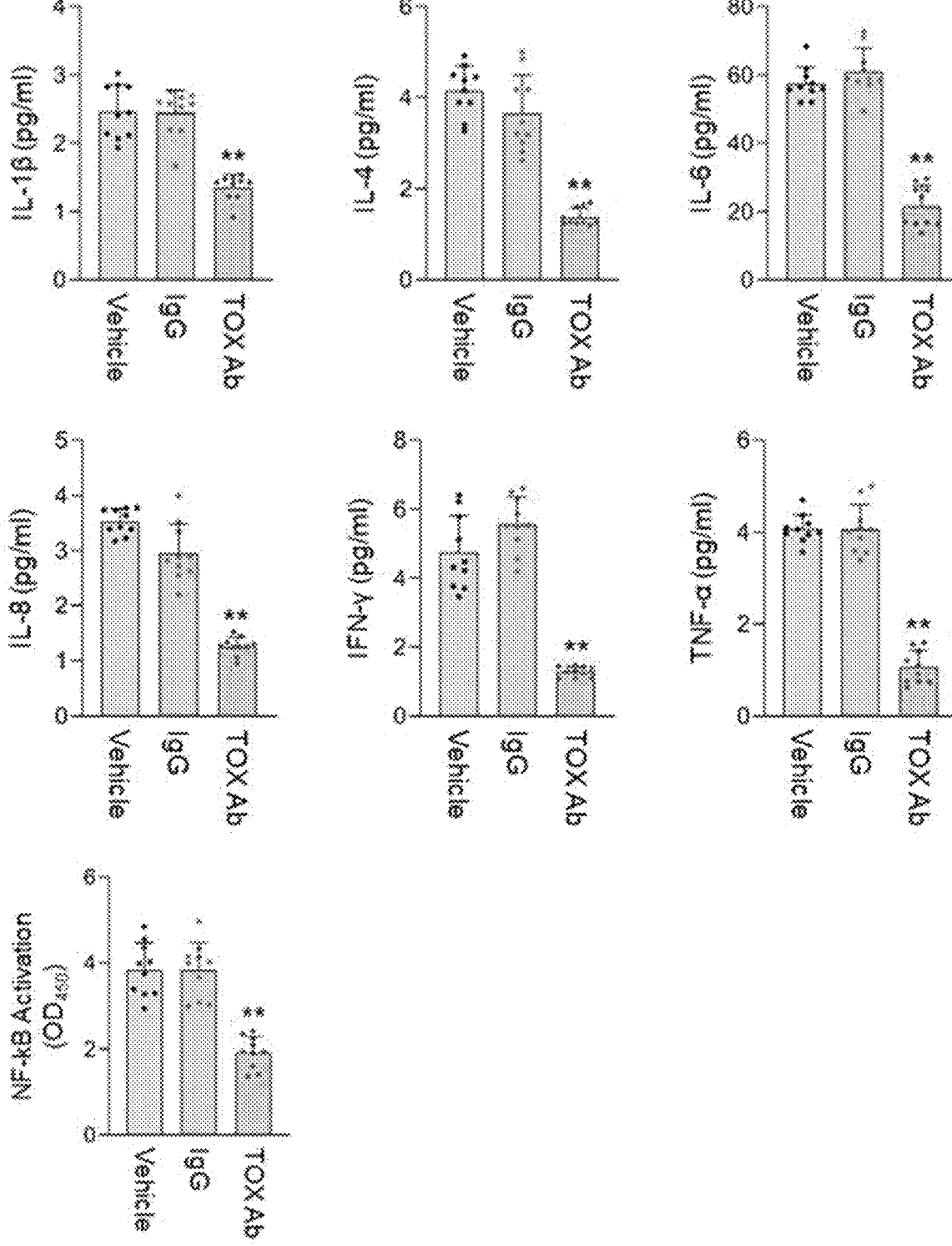
FIG. 7 shows the results of examining effects of inhibiting the production of various cytokines and the activation of NF-κB in PBMCs separated from the blood of COVID-19 patients according to an example of the present disclosure.

As a result, as shown in FIG. 7, the treatment of PBMCs isolated from the patients with SARS-CoV-2 infectious disease showed an effect of inhibiting the secretion of various cytokines including IL-1β, IL-4, IL-6, IL-8, IFN-γ, and TNF-α and the activation of NF-κB.

These results indicate that TOX protein had a great effect on the reduction of inflammation reaction caused by SARS-CoV-2 infection.

Example 4: in Vivo TOX Effect

TOX antibody (ab237009) was administered to mice with abdominal sepsis induced by cecal ligation and puncture (CLP), and the survival rate of the mice was checked.

Specifically, C57BL/6 male mice (6-7-weeks-old, weighing 18-20 g) were purchased from Orient Bio and used after an acclimatization period of 12 days. Five mice per cage were raised with a 12:12 hour light/dark cycle in an environment of a temperature of 20-25° C. and a humidity of 40-45%. The mice were given a normal rodent diet, and water was freely supplied (ad libitum). Any animal was treated according to the Guide for Care and Use of Laboratory Animals published by KRIBB No. 1305021.

The CLP-induced sepsis mouse model was prepared with reference to Nat Protoc 4, 31-36 (2009). A2 cm midline incision was made to expose the cecum and adjoining small intestine. The cecum was then ligated tightly using 5.0 mm of a 3.0-silk suture from the cecal tip, punctured with a 22-gauge needle, and then gently squeezed to extrude feces from the perforation site. The cecum was then returned to the peritoneal cavity, and the laparotomy site was sutured using 4.0-silk. For sham operations, the cecum of the mice was surgically exposed, but not ligated or punctured, and then returned to the abdominal cavity.

The TOX antibody was administered two times (100 ng/ml or 200 ng/ml) 12 and 36 hours after CLP, and then the survival rate was checked every six hours. The blood was collected at 72 hours to investigate organ damage biomarkers in the blood. In addition, H&E staining was performed to investigate the lung tissue damage.

Figure 8:
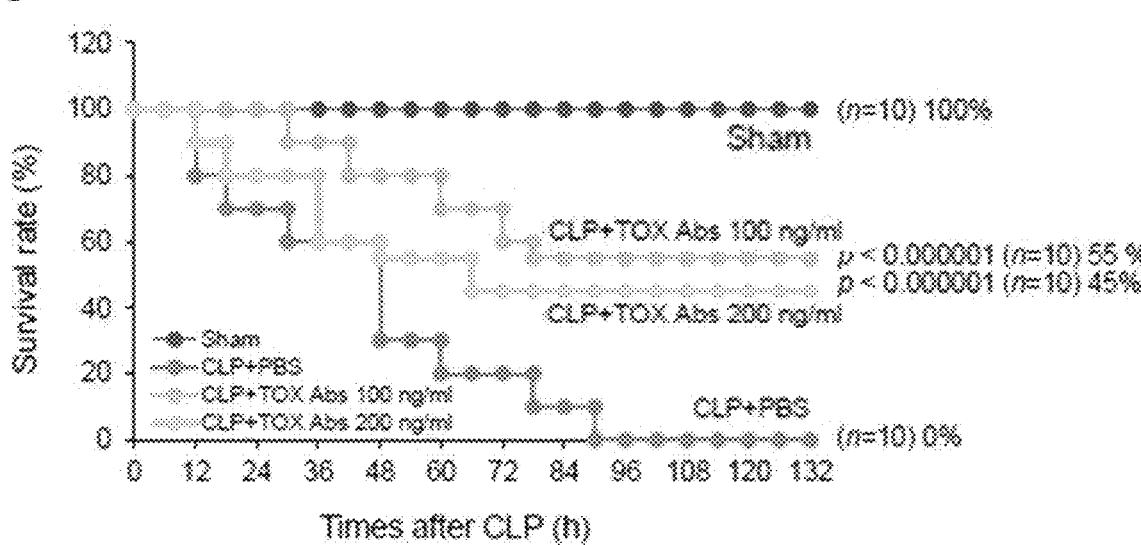
FIG. 8 shows the results of examining the survival rate of a CLP-mouse model by TOX antibody treatment according to an example of the present disclosure.
Figure 8:
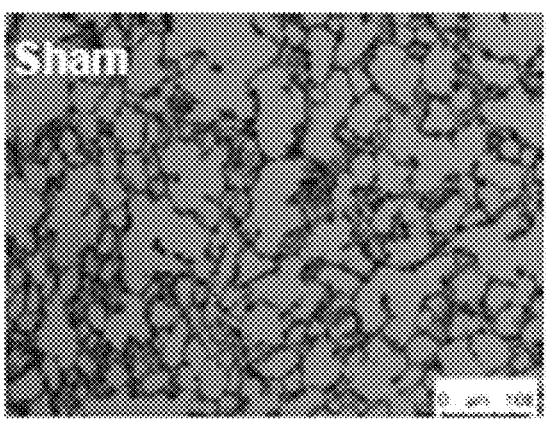
Figure 8:
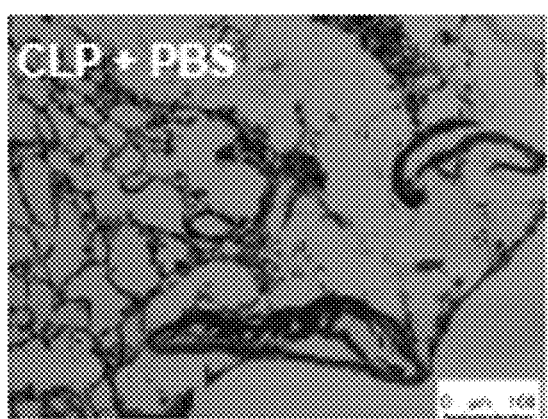
Figure 8:
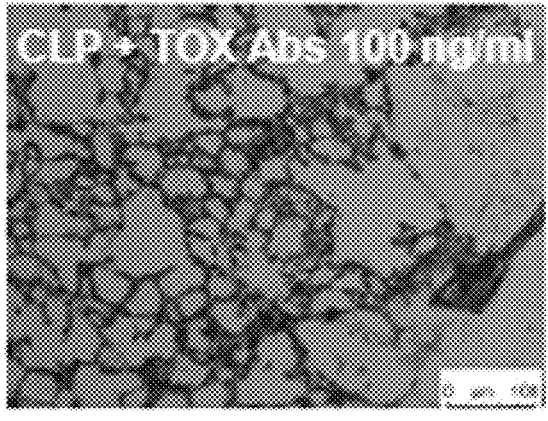
Figure 8:
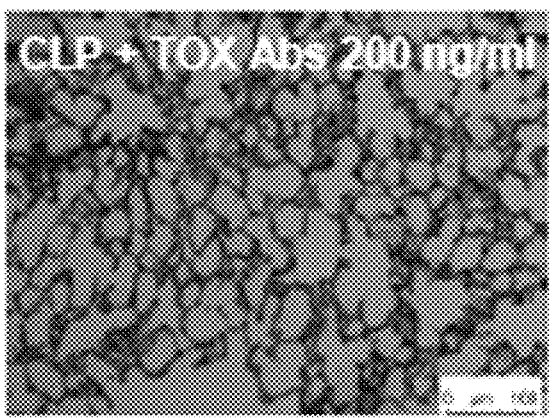

As a result, as shown in FIG. 8, the survival rate was increased (45-55%) in the mice receiving TOX antibody.

These results indicate that TOX antibody had a great effect in the treatment of sepsis caused by SARS-CoV-2 infection.

---

---

What is claimed is:

1. A method for treating SARS-CoV-2 infectious disease accompanied by sepsis or acute respiratory distress syndrome (ARDS) in a subject in need thereof, the method comprising administering to the subject a therapeutically effective amount of a TOX-directed inhibitory agent selected from the group consisting of: (i) an antibody or antigen-binding fragment that specifically binds thymocyte selection-associated high mobility group box (TOX) protein comprising SEQ ID NO: 1; and (ii) an siRNA or shRNA that specifically hybridizes to a polynucle-
otide comprising SEQ ID NO: 2 encoding human TOX.

2. A method for treating a patient infected with SARS-
CoV-2 and accompanied by sepsis or acute respiratory
distress syndrome (ARDS), the method comprising:

obtaining a biological sample from the patient;

measuring TOX protein level or TOX mRNA expression
level in the biological sample;

comparing the measured TOX protein level or TOX
mRNA expression level with that of a normal control
group;

determining that the measured TOX protein level or TOX
mRNA expression level is at least two-fold higher than
that of the normal control group; and administering to the patient a therapeutically effective
amount of a TOX-directed inhibitory agent selected
from the group consisting of: (i) an antibody or antigen-
binding fragment that specifically binds thymocyte
selection-associated high mobility group box (TOX)
protein comprising SEQ ID NO: 1; and (ii) an siRNA
or shRNA that specifically hybridizes to a polynucle-
otide comprising SEQ ID NO: 2 encoding human TOX.

3. The method of claim 2, wherein the biological sample
is at least one selected from the group consisting of blood,
plasma, serum, saliva, nasal mucus, sputum, capsular fluid,
amniotic fluid, ascites, cervical or vaginal discharge, urine,
and cerebrospinal fluid.

* * * * *